United States Patent [19]

Huang et al.

[11] Patent Number: 5,424,301

[45] Date of Patent: Jun. 13, 1995

[54] STARCH STABILIZED O-SUBSTITUTED TETRAHYDROPYRIDINE OXIME CHOLINERGIC AGENTS

[75] Inventors: Hua-Pin Huang, Succasunna; Scott C. Wootton, Liberty Corner; Thomas N. Julian, Annandale; Galen W. Radebaugh, Chester; Mahdi B. Fawzi, Flanders, all of N.J.

[73] Assignee: Warner-Lambert Company, Morris Plains, N.J.

[21] Appl. No.: 12,108

[22] Filed: Feb. 1, 1993

[51] Int. Cl.[6] ............................................. A61K 31/715
[52] U.S. Cl. .......................................... 514/60; 514/54; 514/333; 514/334; 514/335; 514/357; 514/778; 514/879; 514/960; 514/970; 514/972
[58] Field of Search ................ 514/54, 60, 960, 970, 514/972, 778, 879, 357, 333, 334, 335

[56] References Cited

U.S. PATENT DOCUMENTS

| | | | |
|---|---|---|---|
| 3,446,894 | 5/1969 | Magid | 424/465 |
| 3,523,871 | 8/1970 | Matsuoka et al. | 514/54 |
| 3,533,871 | 10/1970 | Zentmyer | 156/205 |
| 4,268,265 | 5/1981 | Von Wattenwyl | 424/452 |
| 4,710,517 | 12/1987 | Umezawa et al. | 514/616 |
| 4,786,648 | 11/1988 | Bergmeier et al. | 514/357 |
| 4,812,445 | 3/1989 | Eden et al. | 514/60 |
| 4,824,938 | 4/1989 | Koyama et al. | 530/351 |
| 4,837,241 | 6/1989 | Jensen et al. | 514/340 |

FOREIGN PATENT DOCUMENTS 0391400 10/1990 European Pat. Off. .

OTHER PUBLICATIONS

AN 80-35636c [20] WPIDS; JP 55047615; Apr. 4, 1980.

*Primary Examiner*—Ronald W. Griffin
*Attorney, Agent, or Firm*—Michael J. Atkins

[57] ABSTRACT

Solid compositions of certain cholinergic compounds are stabilized in starch. Especially compositions of corn starch combined or mixed with the O-substituted-1,2,5,6-tetrahydro-3-pyridine oxime ether, CI-979 HCl, a cognition activator, have been found stable in a heated environment of up to 60° C. over 17 days such that no losses were detected by HPLC analysis. A solid peroral pharmaceutical formulation for the treatment of cognitive disorders is based on the bicomponent composition of active ingredient and stabilizer using appropriate amounts of other excipients or components known in the formulation art.

15 Claims, 1 Drawing Sheet

STARCH STABILIZED O-SUBSTITUTED TETRAHYDROPYRIDINE OXIME CHOLINERGIC AGENTS

FIELD OF THE INVENTION

The present invention relates generally to a stabilized solid composition comprising starch for an improved shelf life of cholinergic agents and, more particularly, certain O-substituted 1,2,5,6-tetrahydro-3- or 1,2,3,6-tetrahydro-4-pyridine oxime ethers, such as the cognition activator, CI-979 HCl.

BACKGROUND OF THE INVENTION

Disorders of cognition are generally accompanied by symptoms of forgetfulness, confusion, memory loss, and other aspects as a result of aging, brain injury or disease. The concomitant decrease in cognitive function during the aging process has been documented in various mammals and more recently in human subjects as well. In particular, presenile and senile primary degenerative dementia appear to be common causes of mental deterioration among the elderly. In fact, the symptoms of cognitive disorder appear to be associated with decreased acetyl choline synthesis as well as impairment of the choline receptive neurons. Especially, the activity of the enzyme choline acetyl transferase (CAT) which catalyzes the synthesis of acetyl choline from its previous choline and acetyl coenzyme A can be severely reduced as reflected by the loss of cholinergic (acetyl choline releasing) nerve endings in the hippocampus. The cholinergic terminals are recognized as critically important to memory function.

The alkaloid arecoline, e.g. methyl 1-methyl-1,2,5,6-tetrahydropiperidine-3-carboxylate, derived from *Areca catechu* (betel nut) is a natural cholinergic agonist of short biological half-life with both central and peripheral muscarinic effects. Arecoline is however toxic in mammalian systems and limited to veterinary anthelmintic use.

O-substituted tetrahydropyridine ether oximes are alkaloid derivatives known to have pharmacological properties that make them useful as cholinergic agents. In particular, the preferred compound CI-979 is a newly discovered cognition activator as described in U.S. Pat. No. 4,786,648 to Bergmeier, et al, which disclosure is incorporated by reference in the present specification. Therefore, the drug CI-979 HCl has been under consideration for therapy of age-associated memory impairment and primary degenerative dementia. Furthermore, the cognition activator CI-979 HCl is being developed for the treatment of Alzheimer's disease.

Specifically, CI-979 has the following structural formula (Ia):

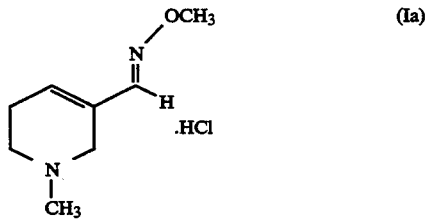
(Ia)

As can be seen in formula (Ia), CI-979 contains a methyloxime group attached to the basic tetrahydropyridine ring to form 1,2,5,6-tetrahydro-1-methyl-3-pyridine methyloxime. Similar to other pyridine derivatives, the free base form of CI-979 is a volatile oily liquid, whereas CI-979 monohydrochloride is obtained as a stable white crystalline salt.

In the course of preformulation studies, the storage stability of the drug has been tested by exposure to heat, UV light, and extremes of the pH range. Specifically, it has been found that the HCl salt is converted in the presence of basic or neutral excipients and even minute amounts of moisture to the volatile free base form that consequently evaporates. Furthermore, in acidic environments of less than about pH 5 the drug undergoes hydrolysis to an aldehyde degradation product of CI-979. See FIG. 1, compound (A). The acid hydrolyzed products of the drug CI-979 HCl are virtually devoid of biological activity.

As illustrated in FIG. 1, two major degradation pathways have been proposed for CI-979 HCl. One pathway represents the hydrolysis to the aldehyde compound (A), 1,2,5,6-tetrahydro-1-methyl-3-pyridine carboxaldehyde, under acidic (i.e. <pH5) conditions.

The second pathway consists of isomerization to the syn- (or Z-) isomer of CI-979 by exposure to UV light.

In particular, hydrolysis of CI-979 to the aldehyde form is a temperature dependent first-order reaction. The light-catalyzed reaction of CI-979 HCl in solution is apparently somewhat pH-dependent, with the highest rate of isomerization occurring at about pH 8.0. The UV light energy presumably weakens the oxime double bond and potentiates rotation to a thermodynamically less stable state.

Moreover, the alkaloid drug, CI-979 HCl, has been found to be labile in acidic and neutral, even in the solid state with only slightly humid microenvironments, microenvironment being defined as the ambient conditions surrounding a given molecular aggregate or agglomerate. In fact, CI-979 HCl undergoes hydrolysis as a solid mixture formulated in bulk with polyhydroxy excipients. However, only minimal isomerization has been observed as measured by reverse phase high performance liquid chromatography.

Consequently, the storage stability problem of the drug as a solid formulation represented a two-fold dilemma. On the one hand, an acid microenvironment would cause hydrolysis of CI-979 HCl, although preventing conversion of the HCl-salt to the free base and subsequent volatilization. On the other hand, a neutral or alkaline microenvironment would diminish CI-979 degradation but allow formation of the volatile free base of the drug.

Plant derived polysaccharides such as starch are used by the skilled in the art as diluent, binder or disintegrant material in solid dosage forms. U.S. Pat. No. 4,812,445 discloses a process for encapsulating materials in the matrix of aqueous starch slurries. U.S. Pat. No. 4,786,648 discloses the use of polysaccharides such as dextrose and starch as carrier or binder material in tablets and powders. U.S. Pat. No. 3,523,871 reports a process for stabilizing the enzyme catalase by the use of soluble starch (inter alia) in order to obtain a stable, homogeneous and non-hygroscopic preparation.

Notwithstanding the well-known uses of starch and similar neutral polysaccharides in pharmaceutical preparations, stabilization for improved shelf life of the subject oximes having the aforedescribed two-fold lability has remained a problem.

It is therefore the object of the present invention to provide a solid composition for stabilizing certain alkaloid methyloximes, such as the cognition activating agent, CI-979 HCl for use in the treatment cognitive disorders. In particular, it is the object of the present invention to provide triturate of the drug in a solid neutral excipient such as starch which simultaneously avoids hydrolytic degradation and neutral/base volatilization of the alkaloid drug.

It is the further object of the present invention to provide a method of preparing a solid starch composition stabilizing the cholinergic alkaloid methyloximes such as the cognition activator, CI-979 HCl.

SUMMARY OF THE INVENTION

It has now been discovered that O-substituted tetrahydropyridine oximes can be stabilized in mixtures with starch or similar polysaccharides, exhibiting a neutral pH range. Moreover, the present invention comprises a process for stabilizing the alkaloid ether oximes by trituration with starch or similar neutral polysaccharides.

Therefore, the present invention provides a means for stabilizing certain O-substituted 1,2,5,6-tetrahydropyridine oximes in a solid composition comprising low concentrations of the cholinergic alkaloid drug admixed with or triturated in stabilization effective amounts of starch or similar neutral polysaccharides.

In particular, the present invention provides a stable solid bicomponent composition containing a cognition activator, such as CI-979 HCl of the above described structural formula, and a polysaccharide material, such as corn starch.

A preferred embodiment of the present invention provides a stable peroral pharmaceutical formulation for the treatment of cognitive disorders in animals and humans, containing the composition of the drug CI-979 HCl in a mixture with or triturate of corn starch at concentrations ranging from about 0.1% (w/w) to about 1% (w/w) and about 5% (w/w) to about 10% (w/w) for each component, respectively.

Another preferred embodiment of the present invention provides a bicomponent mixture or a triturate of CI-979 in corn starch at a dry weight ratio ranging from about 1:20 to about 1:900.

It is further an important aspect of the preferred embodiment of the invention to provide a mixture of CI-979 HCl in starch which is stable at elevated temperatures.

Finally the mixture of CI-979 in starch is useful for stable pharmaceutical formulations.

DETAILED DESCRIPTION OF THE INVENTION

Figure 1:
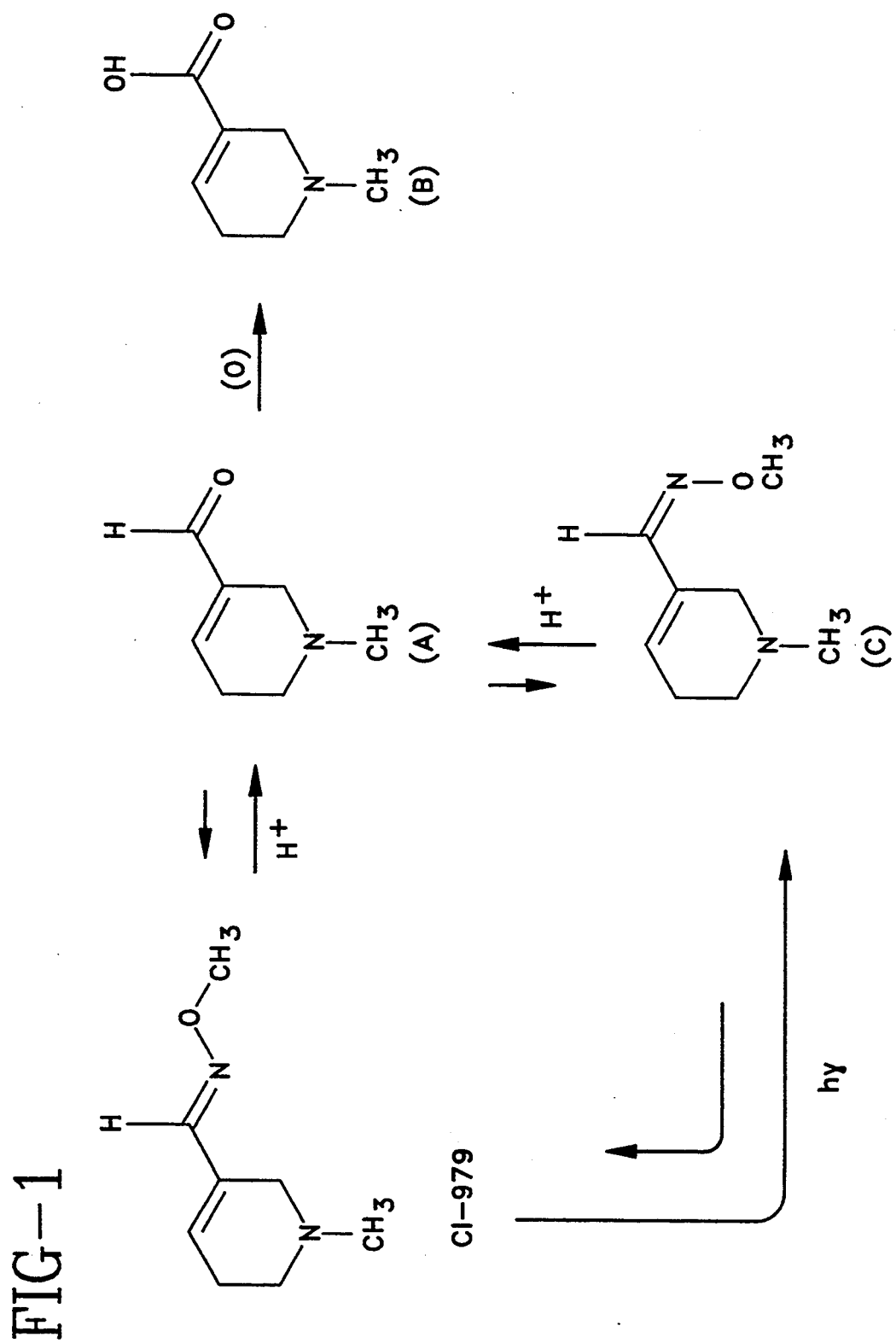
FIG. 1 illustrates a schematic representation of the various putative pathways of degradation.

The chemical properties of the 1,2,5,6-tetrahydropyridine alkaloid derivative, CI-979 HCl of structural formula I, indicate that the compound is labile in both highly acidic and basic as well as neutral environments. Moreover, CI-979 HCl undergoes degradation by acid hydrolysis or free base formation and evaporation not only in solution but also in solid compositions containing certain types of excipients (see Table I). The efficacy or storage stability of a composition containing, e.g., CI-979 HCl, depends upon keeping the compound safe from hydrolytic degradation or conversion to the volatile free base to an aldehyde (A) or carboxylic acid (B) breakdown product. Since the alkaloid content or activity is frequently diminished with time in certain solid blends, suitable excipients are sought which prevent degradation or volatilization of the active ingredient.

The present invention now provides a neutral polysaccharide excipient, starch, in a formulation with CI979 HCl which effectively prevents volatilization of the active compound while simultaneously removing the potential to generate hydrolysis degradation products of CI-979 such as 1,2,5,6-tetrahydropyridine carboxaldehyde or 1,2,5,6-tetrahydropyridine carboxylic acid.

The term "starch" as used herein includes chemically essentially non-modified neutral starches as for example generally carbohydrates of natural, vegetable origin, composed mainly of amylose and/or amylopectin.

TABLE I

| | | | 10 days at 60° C. | | | 17 days at 60° C. | | |
|---|---|---|---|---|---|---|---|---|
| Excipient | pH$_1$ | Initial Assay[2] | % CI-979 Remaining[3] | % aldehyde (A) Present[4] | Total | % CI-979 Remaining[3] | % aldehyde (A) Present[4] | Total |
| Adipic Acid | 2.5 | 101 | 84 | 4 | 88 | 85 | 3 | 88 |
| Fumaric Acid | 2.3 | 100 | 90 | 2 | 92 | 88 | 2 | 90 |
| Succinic Acid | 2.3 | 100 | 64 | 14 | 78 | 71 | 7 | 78 |
| Gentisic Acid | 2.1 | 99 | 69 | 45 | 114 | 61 | 34 | 95 |
| Alginic Acid | 2.7 | 80 | 18 | 65 | 83 | — | — | — |
| Sodium Phosphate Monobasic | 3.3 | 99 | 44 | 35 | 79 | 23 | 35 | 58 |
| PVP K29/32 | 4.0 | 100 | 78 | 0 | 78 | 73 | 0 | 73 |
| Lactose, Anhydrous NF | 4.5 | 101 | 87 | 0 | 87 | 84 | 0 | 84 |
| Sugar granular NF | 5.2 | 102 | 87 | 2 | 89 | 83 | 2 | 85 |
| Non-pareil Seeds | 5.7 | 99 | 74 | 0 | 74 | 89 | 0 | 89 |
| Eudragit L100 | 5.8 | 99 | 62 | 14 | 76 | — | — | — |
| Avicel PH 101 | 5.9 | 71 | 110 | 0 | 110 | — | — | — |
| HPβCD (Encapsin) | 6.2 | 101 | 96 | 0 | 96 | 95 | 0 | 95 |
| Corn Starch NF | 6.3 | 98 | 95 | 0 | 95 | 92 | 2 | 94 |
| Sephadex G50 | 6.5 | 93 | 75 | 0 | 75 | 11 | 0 | 11 |
| HPC (Klucel EF)[5] | 7.1 | 100 | 57 | 0 | 57 | 55 | 0 | 55 |
| Sodium Phosphate Dibasic | 8.9 | 102 | 4 | 0 | 4 | 2 | 0.5 | 2.5 |

TABLE I-continued

Recovery of CI-979 HCl after storage at 60° C. for 10 and 17 days

| | | | 10 days at 60° C. | | | 17 days at 60° C. | | |
|---|---|---|---|---|---|---|---|---|
| Excipient | pH₁ | Initial Assay² | % CI-979 Remaining³ | % aldehyde (A) Present⁴ | Total | % CI-979 Remaining³ | % aldehyde (A) Present⁴ | Total |
| Carrageenan | 10.1 | 63 | 7 | 0 | 7 | — | — | — |

¹pH of a saturated aqueous suspension of the excipient alone. For PVP, Klucel and carrageenan, the pH was determined before they became too viscous (ca. 5 to 10%).
²% CI-979, based on theoretical value.
³Based on initial assay
⁴Based on the maximum theoretical amount that could be formed.
⁵HPC = Hydroxypropyl cellulose.

They may be extracted from various plants, examples being potatoes, rice, tapioca, corn (maize), pea, and cereals derived from grains such as rye, oats, wheat. Preferred according to present invention is starch made from potatoes, corn or rice. It further includes physically modified neutral starches such as gelatinized or cooked starches.

Comparative tests demonstrated that basic or neutral excipients cause the HCl salt of the drug CI-979 to convert to the volatile free base which subsequently evaporates. In a solid composition comprising an acidic excipient as stabilizer, the drug still may undergo some hydrolysis to an aldehyde degradation product, under conditions described in Table I (at 60° C. for 10 days and 17 days, respectively) at normal, ambient atmospheric conditions which contribute a minimal amount of moisture. The putative pathway indicated in FIG. 1. In particular, the CI-979 may undergo acid hydrolysis to form the carbon aldehyde degradation product (A) and even further the carboxylic acid form (B). Both forms, (A) and (B) are completely inactive. At neutral and basic conditions the alkaloid salt drug converts to the oily volatile free base of CI-979 and may therefore evaporate. Upon exposure to U.V. light radiation, the drug converts to its inactive Z-isomer (C).

The pre-formulation compatibility tests of various excipients for use in drug triturates revealed upon analysis a loss of mass balance of the solid composition at high temperatures (60° C.). This loss of mass balance was not observed when the drug was incubated alone at this elevated temperature. The quantities are as described below (Example 1).

In order to test the comparative stability afforded to the drug by various excipients under accelerated conditions the following drug compatibility study was conducted as in experimental Example 1. The comparative data in Table I show that corn starch significantly minimizes the loss of drug through evaporation or hydrolytic degradation. Even under the accelerated stress conditions at high temperatures as described below (Table I) CI-979 was found stable when combined or triturated with corn starch. This advantageously stabilizing effect of corn starch is in surprising contrast to the fact that other excipients in two-component studies under similar conditions of pH, temperature and liquidity did not prevent significant losses of CI-979 from various formulations. Bicomponent triturates of CI-979 HCl with different excipients are assayed upon storage at about 60° C. a week or more are listed in Table I.

EXAMPLE 1

Example 1 relates to a comparative two-component drug compatibility study using various excipients and testing the resulting stability under accelerated conditions, shown in Table I. Excipients used included: a) adipic acid, b) fumaric acid, c) succinic acid, d) gentisic acid, e) alginic acid, f) sodium phosphate monobasic, g) PVP, h) lactose, anhydrous, i) sugar, granular, j) nonpareil seeds k) eudragit, l) avicel, m) hydroxy β-cyclodextrin (HPβCD), n) corn starch, o) sephadex G50, p) hydroxypropyl cellulose (HPC), q) sodium phosphate, dibasic, and r) carrageenan.

In fact, the amount of the aldehyde degradation product (A) was less than 1% (w/w) in all cases. These advantageously stable complexes, therefore, can be predicted to allow further optional variations of the solid storage formulation of CI-979 HCl.

An aliquot of the drug solution containing 0.5 mg of CI-979 HCl was admixed with triturated in about 200 mg of excipient and placed in an oven of 60° C. for 10 and 17 days. To ensure good mixing of the drug in the excipient, all the excipients were ground and passed through a #80 mesh screen prior to mixing. The pH values of a saturated or 20% aqueous solution and/or suspension of the excipients are also listed in Table I as an approximate indicator of the pH conditions of the various CI-979 mixtures. Table I also indicates the percent by weight of CI-979 remaining in any one composition and the CI-979 aldehyde breakdown product generated from CI-979 HCl as determined by reverse phase high performance liquid chromatography (HPLC). The HPLC procedure described below was used to measure the concentrations of CI-979 and the breakdown products of stored formulations of the drug. The HPLC system consisted of a Hewlett-Packard 1090 Liquid Chromatograph equipped with Beckman Digimetry MKS Instrument Coupler and a Kratos model 783 detector operated at a fixed wavelength of 225 nm. The column bed was Zorbax CN, 5 mm, 250 mm×4.6 mm i.d. An aqueous buffer of 0.001M Pic B8 ® (octanesulfonic acid), 0.00025M Triethylamine was adjusted to pH 3.0 with $H_3PO_4$ and modified with Acetonitrile in the mobile phase to 99:1 ratio (Buffer: Modifier) with an eluant flow rate of 1.3 ml/min for 15 min run time. The injection volume was 20 μl. The retention times were found approximately 3.8 min for (B)(see FIG. 1) or 1,2,5,6-tetrahydro-1-methyl-3pyridine carboxylic acid, 4.6 min for (A) or 1,2,5,6tetrahydro-1-methyl-3-pyridine carboxaldehyde, 9.6 min for the (C) or the Z-isomer of CI-979, and 10.5 min for CI-979.

A standard reference solution of analytically pure CI-979 HCl was prepared at a final concentration of 0.02 mg/ml. Samples were prepared by weighing aliquots of approximately 100 mg of the CI-979 HCl/excipient mixture (equivalent to approximately 1.0 mg CI-979 HCl), dissolving it in water and diluting the solution to a concentration of about 0.02 mg/ml. (See FIG. 3 for a representative chromatogram of a CI-979 HCl standard preparation.) For drug/dibasic sodium phosphate samples, 1N HCl was used to dissolve the drug and to neutralize the sample solution. Samples that were not soluble in water were filtered through a 0.45 μm syringeless glass microfiber filter (Genex, Inc.) before HPLC assay. The drug was shown not to adsorb to the filter. Interference from soluble excipients in the sample solutions was not observed in any of the HPLC chromatograms. Percent CI-979 remaining was calculated with reference to initial values. Percent of the aldehyde breakdown product (A) (see FIG. 1) was calculated based upon the maximum theoretical amount that could be formed if 100% of the parent compound was hydrolyzed. The quantities (w/w percent) of CI-979 remaining after storage, with different solid excipients, are listed in Table I. The pH values,.of a saturated solution of the excipients are also listed in Table I.

Surprisingly, corn starch provided the best recovery of the alkaloid drug among the excipients studied, especially compared to excipients with similar pH values. In fact, starch as neutral excipient provided surprisingly better stability for CI-979 HCl as compared to certain acidic excipients.

EXAMPLE 2

Samples of approximately 100 mg of the CI-979 HCl/excipient mixture containing about 1.0 mg CI-979 HCl were preferred as aqueous solutions of 0.02 mg mixture/ml in order to assay the presence of CI-979 HCl by reverse phase high performance liquid chromatography (HPLC).

The test results listed in Table I show that when CI-979 HCl was incubated in the presence of various excipients, which are known in the art, the drug loss at 60° C. was not measurable in terms of aldehyde formation. In particular, most compositions with neutral or basic excipients revealed a significant drug loss without a significant increase in hydrolysis product. It is presumed that this observed loss is due to a neutralization reaction of CI-979 HCl followed by volatilization of the free base.

In view of the comparison study, certain mono or polyhydroxy excipients may aid in the conversion of CI-979 HCL to its free base. Without wishing to engage in theoretical speculation, it appears that the free base formation and subsequent volatilization derives from intermolecular interactions of CI-979 HCl with polar groups of the excipients. The presence of highly polar functional groups (carbonyl, hydroxyl, amino) in neutral excipients may afford such strong neutralization capability as to preclude the exposure of solid CI-979 hydrochloride/excipient compositions to elevated temperatures. The experiments showed that the useful ranges of the starting materials for effectively stabilized solid formulations of CI-979 HCl are about 0.001% (w/w) to about 10% (w/w) of CI-979 HCl and about 1% (w/w) to about 99% (w/w) of corn starch. The preferred embodiment may include compositions of about 0.1% (w/w) to about 1% (w/w) Of CI-979 HCl and 5% (w/w) to about 50% (w/w) of corn starch.

Since starch is commonly used as a diluent, a binder or a disintegrant, it is all the more surprising that during aggravated storage conditions at neutral pH, a corn starch combination with the alkaloid drug would not only effectively prevent acid hydrolysis but also the loss of activity by volatilization. A stable mixture of CI-979 HCl corn starch can thus be prepared and subjected to further formulation. Stable mixtures of CI-979 HCl and corn starch may be also prepared in the form of triturate compositions. Further formulation of starch stabilized mixtures of CI-979 HCl may include the use of other excipients typically used in the art of formulating pharmaceutical dosage forms. The types of excipients may include, but not be limited to, binders, lubricants, disintegrants and, diluents. Specific examples of these excipients are listed in the USP XXI/NFXVII, 1990.

For example, admixtures known as useful are crystalline cellulose, hydroxy-propylcellulose, methylcellulose, hydroxypropyl-methylcellulose, polyvinylpyrroledone and similar appropriate amounts of pharmacologically acceptable carriers, vehicles, diluents.

Other possible and supplemental ingredients such as preservatives, driers, glidants, or colorants known as conventional by those skilled in the art may be included optionally in the inventive formulation.

Further to the present invention, microcrystalline cellulose and hydrous lactose may be applied as suitable diluents. In addition, the inventive composition contains a suitable amount of croscarmellose sodium as functional disintegrant. The nonionic detergent Tween 80 or a polyoxyethylene-polyoxypropylene copolymer is used as a surfactant. The composition may also contain hydroxypropyl cellulose as binder selected from among several applicable substances such as, i.e., polyethylene glycol, polyvinylpyrrolidone, polyvinyl alcohol, hydroxymethylcellulose or hydroxypropylmethylcellulose. Further, the preferred formulation may include povidone (1-ethenyl-2-pyrrolidinone polymers) as a dispersing or suspending agent. Magnesium stearate can be selected from a group including other substances such as calcium stearate, stearic acid, palmitic acid, talc or similar lubricating compounds. As anti-oxidants, reagents such as butylated hydroxyanisole, sodium ascorbate, ascorbic acid or others may optionally be incorporated in the composition. A typical example formulation is illustrated below (Example 3; Table II); the Example is given to demonstrate useful pharmaceutical formulations that are based on the stabilized compositions of CI-979 HCl for the treatment of cognitive disorders such as Alzheimer's disease. The appropriate concentrations are indicated in compositions A, B, C and D as listed in Table II.

TABLE II

| Component | Percent by weight Formulation | | | |
| --- | --- | --- | --- | --- |
| | A | B | C | D |
| CI-979 HCl | .001 | .01 | .05 | 1 |
| Corn Starch | 77 | 60 | 70 | 50 |
| Croscarmalose | 1 | 1 | 3 | 2 |
| Microcrystalline cellulose | 20 | | 20.95 | |
| Lactose | | 31.99 | | 42 |
| Povidone | | 5 | | 4 |
| Hydroxypropyl Methylcellulose | | | 4 | |
| Calcium Sterate | | | 2 | |
| Magnesium Sterate | 1.999 | 1 | | |

Considering the stabilizing properties of the solid drug-starch composition it would be deemed within the scope of the present invention as claimed below that other starches such as modified starch, e.g. pregelatinized starch, Novon ® and cellulose derivatives, e.g. ethylcellulose, hydroxypropylethyl cellulose, could also serve to advantageously stabilize CI-979.

What is claimed is:

1. A composition comprising the cognition activating compound, CI-979 monohydrochloride, of formula (Ia):

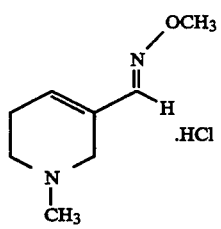

wherein the cognition activating compound is combined in corn starch at concentrations ranging by weight from about 0.001% to about 10% and from about 99% to about 99%, respectively.

2. The composition of claim 1, wherein the cognition activating compound and the corn starch range by weight from about 0.001 to about 1% and from about 5% to about 50%, respectively.

3. The composition of claim 2 wherein the cognition activating compound CI-979 HCl and the corn starch range by weight from about 0.001% to about 1% and from about 5% to about 10%, respectively.

4. The composition of claim 2, wherein the composition is a solid stable at elevated temperatures.

5. A solid bicomponent storage composition having improved shelf life of the cognition activating compound, CI-979 monohydrochloride, of formula (Ia):

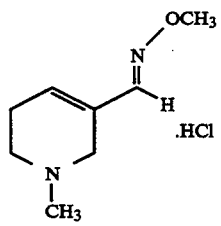

wherein the cognition activating compound is combined in corn starch at concentrations ranging by weight from about 0.001% to about 10% and from about 1% to about 99%, respectively.

6. The solid bicomponent storage composition of claim 5 wherein the cognition activating agent and the corn starch range by weight from about 0.001% to about 1% and from about 5% to about 50%, respectively.

7. A solid peroral pharmaceutical formulation for treatment of impaired cognitive functions in animals and humans comprising the composition of claim 5 wherein, by weight, the CI-979 HCl ranges from about 0.001% to about 1% and the starch ranges from about 1% to about 50%.

8. A method for preparing a solid triturate composition for stabilizing an O-substituted 1,2,5,6-tetrahydropyridine oxime as an active ingredient in a starch comprising the steps:
 (a) mixing at neutral conditions an aqueous solution containing the active ingredient in a starch excipient; and
 (b) drying the composition.

9. The method of claim 8 wherein the active ingredient is a cognition activating compound of formula:

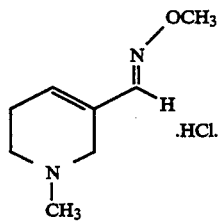

10. The method of claim 8 wherein the solid starch is selected from the group consisting of modified and unmodified starch.

11. A stabilized pharmaceutical formulation for the treatment of age-associated memory impairment comprising a therapeutically effective amount of the cognition activator CI-979 HCl, of formula (Ia):

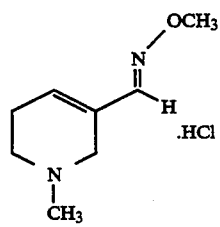

wherein the cognition activating compound is combined in corn starch at concentrations ranging by weight from about 0.001% to about 10% and from about 1% to about 99%, respectively.

12. The pharmaceutical formulation of claim 11 wherein, by weight, the CI-979 HCl ranges from about 0.001% to about 1% and the starch ranges from about 1% to about 50%.

13. The pharmaceutical formulation of claim 12 wherein the formulation further comprises pharmaceutically acceptable inactive excipients selected from the group consisting of carriers, vehicles and diluents.

14. The pharmaceutical formulation of claim 13 wherein the formulation further comprises pharmaceutically acceptable inactive excipients selected from the group consisting of binders, lubricants, disintegrants and diluents.

15. The pharmaceutical formulation of claim 14 wherein the formulation further comprises supplemental ingredients selected from the group consisting of preservatives, driers, glidants and colorants.

* * * * *

UNITED STATES PATENT AND TRADEMARK OFFICE
CERTIFICATE OF CORRECTION

PATENT NO. : 5,424,301
DATED : June 13, 1995
INVENTOR(S) : Hua-Pin Huang, et al

It is certified that error appears in the above-indentified patent and that said Letters Patent is hereby corrected as shown below:

In Claim 1, column 9, line 15, "about 99% to about 99%, respectively" should read -- about 1% to about 99%, respectively--.

Signed and Sealed this

First Day of October, 1996

Attest:

BRUCE LEHMAN

Attesting Officer        Commissioner of Patents and Trademarks